United States Patent
Miettinen et al.

(10) Patent No.: US 12,305,214 B2
(45) Date of Patent: *May 20, 2025

(54) METHOD AND AN APPARATUS FOR INCREASING CONCENTRATION OF SOLUBLE CARBOHYDRATE CONTAINING FRACTION, A SOLUBLE CARBOHYDRATE CONTAINING FRACTION, A SOLID FRACTION AND THEIR USE

(71) Applicant: UPM-KYMMENE CORPORATION, Helsinki (FI)

(72) Inventors: Mauno Miettinen, Lappeenranta (FI); Sami Turunen, Lappeenranta (FI); Juha Tamper, Levänen (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 18/100,411

(22) Filed: Jan. 23, 2023

(65) Prior Publication Data

US 2023/0212618 A1    Jul. 6, 2023

Related U.S. Application Data

(63) Continuation of application No. 15/544,380, filed as application No. PCT/FI2016/050076 on Feb. 5, 2016, now Pat. No. 11,591,624.

(30) Foreign Application Priority Data

Feb. 6, 2015 (FI) ..................... 20155076

(51) Int. Cl.
*C12P 7/10* (2006.01)
*C08H 7/00* (2011.01)
(Continued)

(52) U.S. Cl.
CPC .................. *C12P 7/10* (2013.01); *C08H 6/00* (2013.01); *C08H 8/00* (2013.01); *C12M 45/02* (2013.01);
(Continued)

(58) Field of Classification Search
CPC .... C12P 7/10; C08H 6/00; C08H 8/00; C13K 13/007
See application file for complete search history.

(56) References Cited

U.S. PATENT DOCUMENTS 1,339,489 A    5/1920 Weiss
2002/0164731 A1    11/2002 Eroma et al.
(Continued)

FOREIGN PATENT DOCUMENTS

CN    103917634 A    7/2014
EP    2336194 A1    6/2011
(Continued)

OTHER PUBLICATIONS

Amidon et al., "Biorefinery: conversion of woody biomass to chemicals, energy and materials." Journal of Biobased Materials and Bioenergy 2.2: 100-120 (2008).
(Continued)

*Primary Examiner* — Renee Robinson
(74) *Attorney, Agent, or Firm* — NIXON PEABODY LLP

(57) ABSTRACT

The invention relates to a method and an apparatus for producing a soluble carbohydrate containing fraction (10), in which lignocellulose material (3) formed by treating plant based raw material (1) is conducted into a separation stage (4). The method comprises at least one solid-liquid separation stage (4) for separating a soluble carbohydrate containing fraction (10) and/or a washing filtrate (12) from lignocellulose material (3), and at least a part of the soluble carbohydrate containing fraction (10) and/or the washing (Continued)

filtrate (12) is recirculated to the lignocellulose material (3) for increasing concentration of the soluble carbohydrate containing fraction, and solids (11) and at least a part of the soluble carbohydrate containing fraction (10) are supplied out from the separation stage. Further, the invention relates to the soluble carbohydrate containing fraction and the solid fraction, and their uses.

9 Claims, 9 Drawing Sheets

(51) Int. Cl.
| | | |
|---|---|---|
| *C08H 8/00* | (2010.01) | |
| *C12M 1/00* | (2006.01) | |
| *C12M 1/33* | (2006.01) | |
| *C12N 1/18* | (2006.01) | |
| *C12P 19/02* | (2006.01) | |
| *C13K 13/00* | (2006.01) | |

(52) U.S. Cl.
CPC ............ *C12M 45/09* (2013.01); *C12M 45/20* (2013.01); *C12N 1/18* (2013.01); *C12P 19/02* (2013.01); *C13K 13/007* (2013.01); *C12P 2201/00* (2013.01)

(56) References Cited

U.S. PATENT DOCUMENTS

| | | | |
|---|---|---|---|
| 2009/0056889 A1* | 3/2009 | Ren | C12P 7/10 162/38 |
| 2014/0060522 A1 | 3/2014 | Baynes et al. | |
| 2014/0147904 A1 | 5/2014 | Stubbe et al. | |
| 2015/0167234 A1 | 6/2015 | Von Schoultz et al. | |

FOREIGN PATENT DOCUMENTS

| | | |
|---|---|---|
| GB | 2353730 A | 3/2001 |
| RU | 2012129518 A | 1/2014 |
| WO | 2009080737 A2 | 7/2009 |
| WO | 2013024065 A1 | 2/2013 |
| WO | 2014009604 A1 | 1/2014 |

OTHER PUBLICATIONS

Chaabane et al., "Upgrading the hemicellulosic fraction of biomass into biofuel." Oil & Gas Science and Technology—Revue d'IFP Energies nouvelles 68.4: 663-680 (2013).
Chinese Office Action in Chinese Patent Application No. Cn 201680009107.X, mailed Mar. 5, 2020 (12 pages) (with English translation).
Finnish Office Action in Finnish Patent Application No. FI 20185854, mailed May 29, 2020 (5 pages).
Finnish Search Report in Finnish Patent Application No. FI 20185854, mailed May 29, 2020 (2 pages).
International Search Report from International Application No. PCT/FI2016/050076 dated Apr. 28, 2016.
Karinkanta et al., "Fine grinding of wood—Overview from wood breakage to applications." Biomass and Bioenergy 113: 31-44 (2018).
Office Action in Russian Patent Application No. 2017130700/10, dated May 27, 2019, with English translation (13 pages).
Radlein et al., "A short historical review of fast pyrolysis of biomass." Oil & Gas Science and Technology—Revue d'IFP Energies nouvelles 68.4: 765-783 (2013).
Search Report from U.S. Appl. No. 20/155,076 dated Sep. 3, 2015.
Search Report from Russian Patent Application No. 2017130700/10, dated May 24, 2019, with English translation (4 pages).
Sievers et al., "Performance and techno-economic assessment of several solid-liquid separation technologies for processing dilute-acid pretreated corn stover." Bioresource technology 167: 291-296 (2014).

* cited by examiner

METHOD AND AN APPARATUS FOR INCREASING CONCENTRATION OF SOLUBLE CARBOHYDRATE CONTAINING FRACTION, A SOLUBLE CARBOHYDRATE CONTAINING FRACTION, A SOLID FRACTION AND THEIR USE

CROSS-REFERENCE TO RELATED APPLICATIONS

This application is a continuation of U.S. patent application Ser. No. 15/544,380, filed on Jul. 18, 2017, now allowed, which is a U.S. National Stage of International Application No. PCT/FI2016/050076, filed on Feb. 5, 2016, which claims priority to Finnish Patent No. 20155076, filed Feb. 6, 2015, the contents of each of which are incorporated herein by reference in their entireties.

FIELD OF THE INVENTION

The invention relates to a method and an apparatus for producing a soluble carbohydrate containing fraction and a solid fraction. Further, the invention relates to a soluble carbohydrate containing fraction and its use. Further, the invention relates to a solid fraction and its use.

BACKGROUND OF THE INVENTION

Known from prior art is different methods for forming carbohydrates from different raw materials, such as biomass. Many bio-refinery processes, e.g. hydrolysis, generate lignin and sugars after the treatment of the biomass.

OBJECTIVE OF THE INVENTION

The objective of the invention is to disclose a new method for producing a soluble carbohydrate containing fraction with high concentration. Another objective of the invention is to produce a soluble carbohydrate containing fraction with increased concentration and with improved recovery. Another objective of the invention is to improve fractionation of biomass for producing an improved, concentrated liquid fraction comprising soluble carbohydrates with high recovery and a soluble material free solid fraction.

SUMMARY OF THE INVENTION

According to one embodiment, a method for increasing concentration of a water soluble carbohydrate is disclosed. The method includes separating a washing filtrate and a water soluble carbohydrate containing fraction from a lignocellulose material in a solid-liquid separation stage. The method further includes recirculating a first stream including at least a part of the washing filtrate from the solid-liquid separation stage to the lignocellulose material that is subjected to the solid-liquid separation stage for increasing the concentration of the water soluble carbohydrate. The method further includes recirculating a second stream including at least a part of the water soluble carbohydrate containing fraction from the solid-liquid separation stage to the lignocellulose material that is subjected to the solid-liquid separation stage.

BRIEF DESCRIPTION OF THE DRAWINGS

The accompanying drawings, which are included to provide a further understanding of the invention and constitutes a part of this specification, illustrate some embodiments of the invention and together with the description help to explain the principles of the invention. In the drawings.

DETAILED DESCRIPTION OF THE INVENTION

Figure 1:
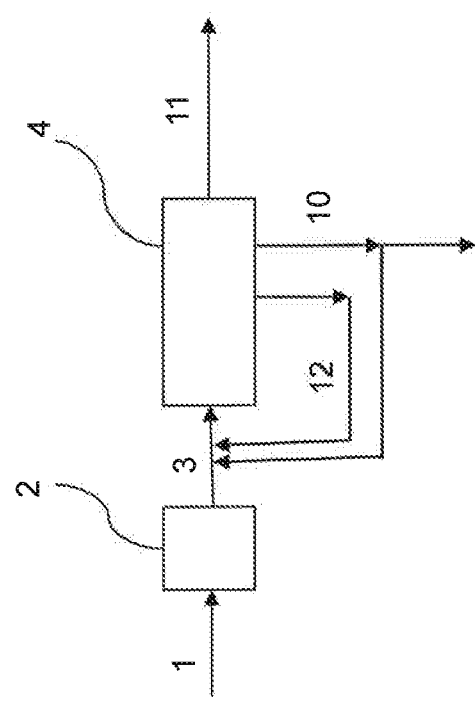
FIG. 1 is a flow chart illustration of a method according to one embodiment of the present invention.

The invention relates to a method for increasing concentration of a liquid fraction comprising soluble carbohydrates, such as a soluble carbohydrate containing fraction, in which lignocellulose material (3) formed by treating plant based raw material (1) is conducted into a separation stage (4,6). In the method of the present invention, the method comprises at least one solid-liquid separation stage (4,6) for separating a soluble carbohydrate containing fraction (10) and/or a washing filtrate (12) from lignocellulose material (3). The separation stage comprises one or more separation steps. At least a part of the soluble carbohydrate containing fraction (10) and/or the washing filtrate (12) is recirculated to the lignocellulose material (3), preferably before a desired separation step of the separation stage (4,6), for increasing concentration of the soluble carbohydrate containing fraction. Solids (11) and at least a part of the soluble carbohydrate containing fraction (10) are supplied out from the separation stage. In one embodiment, at least a part of the washing filtrate (12) is supplied out from the separation stage.

Figure 2:
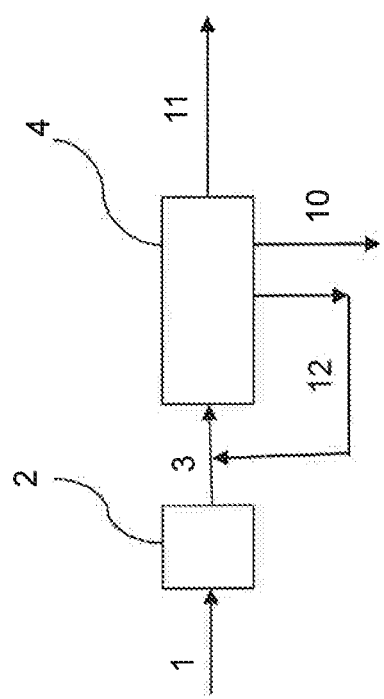
FIG. 2 is a flow chart illustration of a method according to another embodiment of the present invention.
Figure 3:
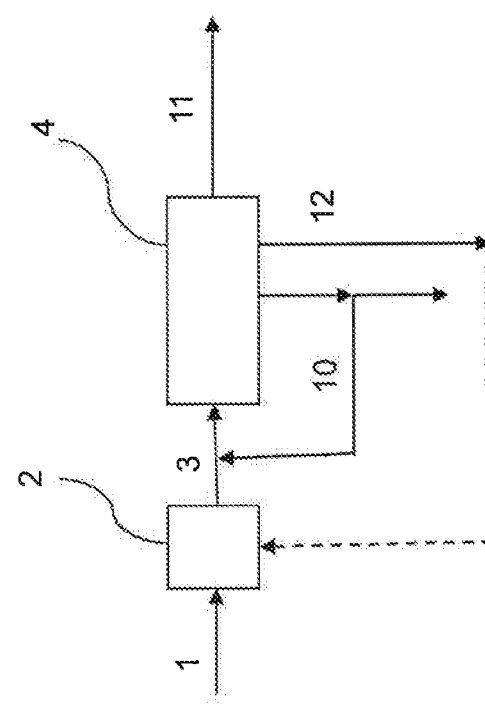
FIG. 3 is a flow chart illustration of a method according to another embodiment of the present invention.
Figure 4:
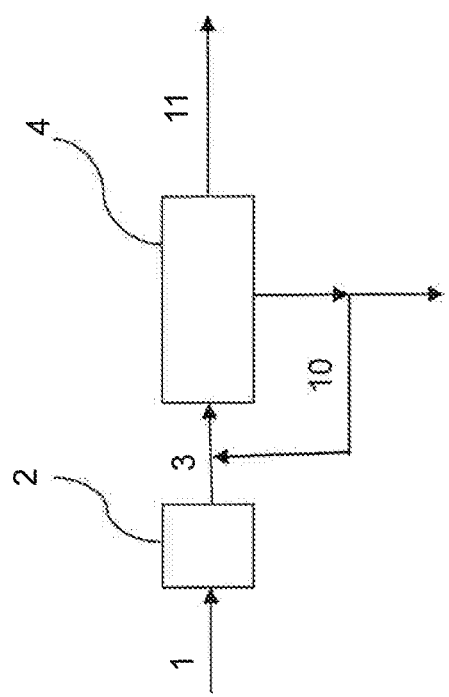
FIG. 4 is a flow chart illustration of a method according to another embodiment of the present invention
Figure 5:
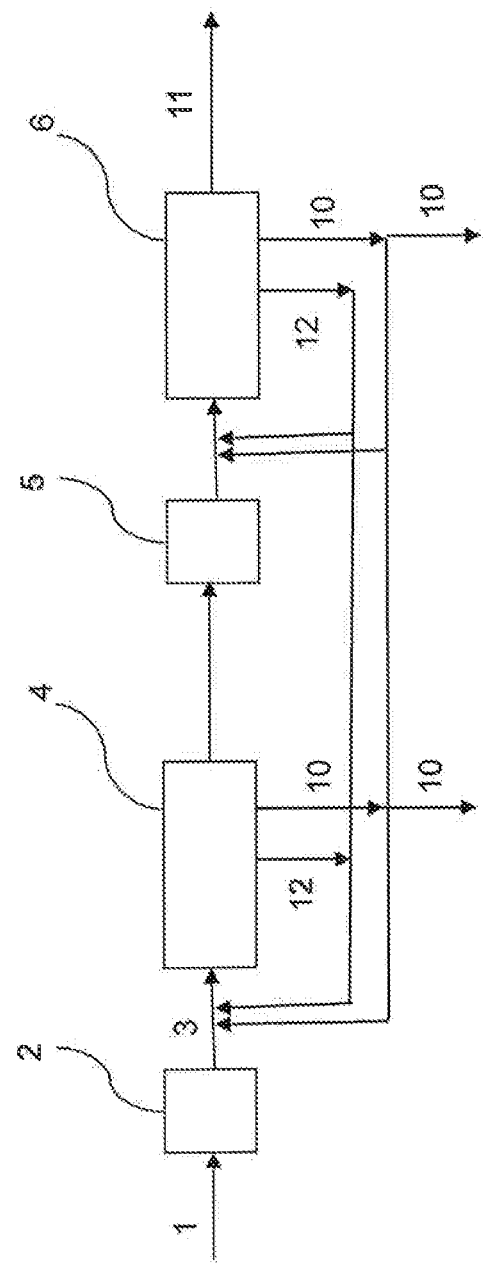
FIG. 5 is a flow chart illustration of a method according to another embodiment of the present invention.
Figure 6:
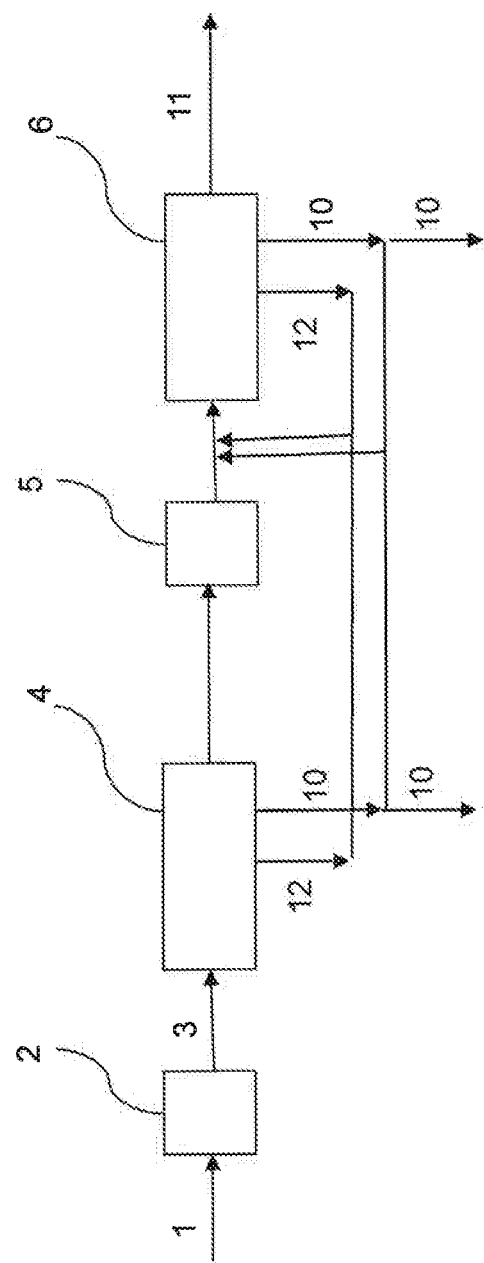
FIG. 6 is a flow chart illustration of a method according to another embodiment of the present invention.
Figure 7:
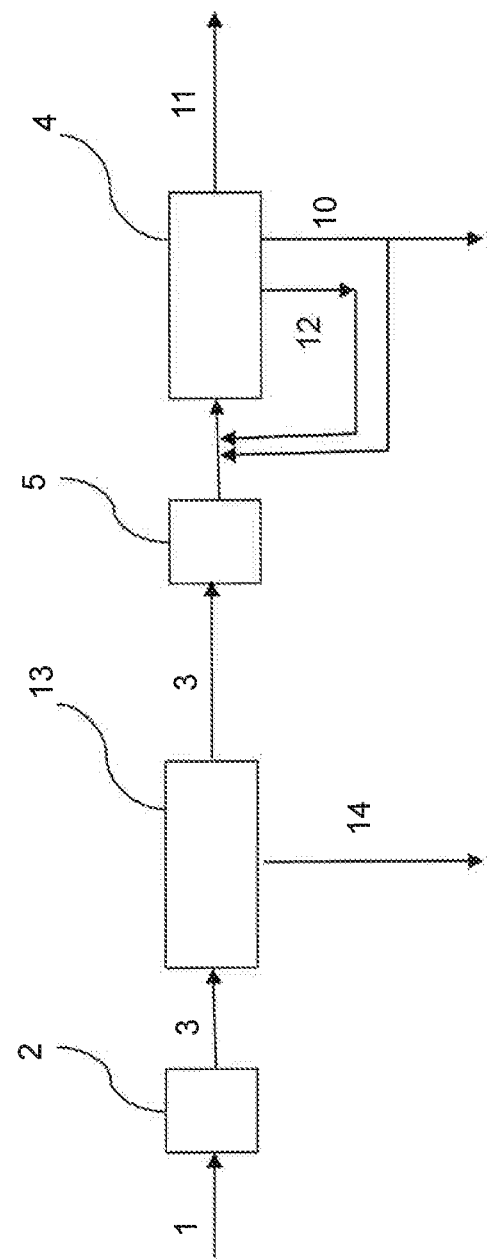
FIG. 7 is a flow chart illustration of a method according to another embodiment of the present invention.

One embodiment of the method of the present invention is shown in FIG. 1. Another embodiment of the method of the present invention is shown in FIG. 2. Another embodiment of the method of the present invention is shown in FIG. 3. Another embodiment of the method of the present invention is shown in FIG. 4. Another embodiment of the method of the present invention is shown in FIG. 5. Another embodiment of the method of the present invention is shown in FIG. 6. Another embodiment of the method of the present invention is shown in FIG. 7.

The apparatus of the present invention comprises at least one solid-liquid separation device (4,6) into which lignocellulose material (3) formed by treating plant based raw material (1) is conducted and in which a soluble carbohydrate containing fraction (10) and/or a washing filtrate (12) are separated from lignocellulose material (3). Further, the apparatus comprises at least one feeding device, such as a pump, for feeding the lignocellulose material (3) into the separation device (4,6). Further, the apparatus comprises at least one recirculation device for recirculating at least a part of the soluble carbohydrate containing fraction (10) and/or the washing filtrate (12) to the lignocellulose material (3), preferably before a desired separation device or separation step, for increasing concentration of the soluble carbohydrate containing fraction. Further, the apparatus comprises means, such as discharge means or outlet means, for supplying solids (11) and at least a part of the soluble carbohydrate containing fraction (10) out from the apparatus. In one embodiment, the apparatus comprises means for supplying at least a part of the washing filtrate (12) out from the apparatus.

The invention is based on a solid-liquid separation. Further, the invention is based on a recirculation of filtrates containing preferably sugars, such as a soluble carbohydrate containing fraction and/or washing filtrate, in order to increase concentration of the soluble carbohydrate containing fraction. In the invention, sugar content of the soluble carbohydrate containing fraction can be increased by means of the recirculation of the filtrates in various applications. Simultaneously, the recovery of the liquid soluble carbohydrate containing fraction can be increased and more pure solid fraction comprising solids can be formed. Further, carbohydrate content and purity of the solids can be increased by means of the present invention. Further, if the washing filtrate is formed so it can be utilized in the process. In one embodiment, small amount of washing is used and thus concentration of soluble compounds can be further increased. In one embodiment, a replacement washing is used which leads to further increase of the concentration of the soluble compounds and increase purity of the solid fraction.

In this context, a washing filtrate means a dilute filtrate from a washing step in which the lignocellulose material is washed. In this context, a soluble carbohydrate containing fraction means a soluble carbohydrate containing filtrate, preferably with high concentration, which is separated from the lignocellulose material. In a preferred embodiment, the washing filtrate and soluble carbohydrate containing fraction include carbohydrates, preferably C5 sugars ($C_5H_{10}O_5$ or $(C_5H_2O)_n$). The soluble carbohydrate containing fraction may be comprise carbohydrates, such as monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or $(C_5H_8O_4)_n$). Preferably, the soluble carbohydrate containing fraction comprises soluble C5 carbohydrates ($C_5H_{10}O_5$ or $C_5(H_2O)_n$) and other carbohydrates. The washing filtrate and soluble carbohydrate containing fraction may comprise also other components. In a preferred embodiment, the solids comprise carbohydrates, and preferably solid C6 carbohydrates ($C_6H_{12}O_6$ or $C_6(H_2O)_n$). The solids may comprise also other carbohydrates and other components.

In this context, plant based raw material means any plant based raw material, e.g. wood based raw material. The plant based raw material includes lignin, cellulose and hemicellulose. In one embodiment, the plant based raw material is selected from the group consisting of wood based raw material, wood, lignocellulose biomass, agricultural residues, bagasse based material, sugarcane bagasse, corn based material, corn stover, wheat straw, rice straw, woody biomass, woody perennials, vascular plants and the like and their mixtures and their combinations. In one embodiment, the plant based raw material is wood based raw material or a mixture comprising wood based material. In one embodiment, the plant based raw material comprises plant pieces, e.g. wood pieces.

In this context, lignocellulose material refers any lignocellulose material which has been formed by treating, such as pre-treating, from the plant based raw material by means of a suitable treatment method in one or more steps. In one embodiment, the lignocellulose material contains carbohydrates and lignin. Preferably, the carbohydrates have $C_n(H_2O)_n$ or $C_n(H_2O)_{n-1}$. The carbohydrates can comprise monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or $(C_5H_8O_4)_n$). Preferably, the lignocellulose material includes carbohydrates, such as soluble C5 carbohydrates ($C_5H_{10}O_5$ or $C_5(H_2O)_n$) and solid C6 carbohydrates ($C_6H_{12}O_6$ or $C_6(H_2O)_n$). The lignocellulose material may contain one or more lignocellulose material components. Preferably, the lignocellulose material is in the form of suspension which contains liquid, such as water. The lignocellulose material (3) is formed from the plant based raw material (1) and is treated in one or more treatment step (2,5). In one embodiment, the lignocellulose material is formed or treated by treatment, preferably by pretreatment, selected from the group consisting of physical treatment, such as milling, extrusion, microwave treatment, ultrasound treatment and freeze treatment, chemical treatment, such as acid treatment, alkaline treatment, ionic liquid treatment, organosolv treatment and ozonolysis, physico-chemical treatment, such as steam explosion treatment, ammonia fiber explosion treatment, $CO_2$ explosion treatment, liquid hot water treatment and wet oxidation, biological treatment and their combinations. Preferably, the plant based raw material is treated to dissolve hemicellulose. In one embodiment, the lignocellulose material is formed or treated by the hydrolysis, e.g. acid hydrolysis, auto-hydrolysis, thermal hydrolysis, enzymatic hydrolysis, supercritical hydrolysis and/or subcritical hydrolysis, in which at least a part of lignin is separated from the raw material in connection with the hydrolysis. In one embodiment, the lignocellulose is formed or treated by the steam explosion, in which hemicelluloses are treated and in which at least a part of polysaccharides of the hemicelluloses degrade into monosaccharides and oligosaccharides. In one embodiment, the lignocellulose material is formed or treated by the hydrolysis and by the steam explosion in one or more steps. In one embodiment, the lignocellulose material is formed or treated by the catalytic pretreatment, e.g. by using acid or base as catalyst. In the pretreatment process the plant based raw material enters the reactor unit where the pretreatment takes place. The lignocellulose material can be treated by means of one or more treatment. The treated lignocellulose material can be then blown to a blowtank. Further, the lignocellulose material can be preferably dewatered, e.g. by dewatering presses in two stages. The dewatering makes possible to separate sugar based streams. In one embodiment, the lignocellulose material consists of fine solid particles. By means of the fine particle size high yields and low amount of degradation may be achieved in the process. Preferably, fine solid particles are fiber-like or indefinable particles smaller than 0.2 mm, or they are particles that are small enough to pass through the Bauer McNett 200-mesh screen. Particle size of the lignocellulose material can be measured, e.g. with an optical measurement device, such as Metso FS5, or a laser diffraction method, such as Coulter LS230. The values for particle size are depending on the method and thus values from Metso FS5 and Coulter LS230 cannot be directly compared. Particle size of the solid particles can be defined based on ISO 16065-N or TAPPI T271. The pretreatment process decreases the particle size and fibre length of original wood fibre, which can be defined by separating fibres by cooking the wood in e.g. sulphate process or maceration. The sulphate process is resulting fibre length of about 80% of the one after the maceration.

In one embodiment, dry matter content of the lignocellulose material is 20-80% by weight after the pretreatment. The dry matter content is determined at 45° C. by means of evaporating. When the determination of the dry matter content is made at temperature 45° C. so also small-molecular organic compounds remain in the mass during the drying of the determination. In one embodiment, the determination of the dry matter content may be done so that it is based, at least partly or as applied, on NREL (National renewable energy laboratory) Laboratory Analytical Procedures for standard biomass analysis determined in the Technical Report NREL/TR-510-48087 (revised July 2011). In one embodiment, the lignocellulose material is diluted with liquid, preferably with water, or steam to form the lignocellulose material feed to the separation stage. In one embodiment, feed concentration of the lignocellulose material is 2-60% by weight, preferably 5-30% by weight, more preferable 10-20% by weight, into a solid-liquid separation stage. If feed concentration of the lignocellulose material is low so then size of the device increases. Preferably, the washing filtrate and/or soluble carbohydrate containing fraction which is recirculated to the lignocellulose material is used in a dilution of the lignocellulose material.

In one embodiment, the lignocellulose material is fed by means of a pump, e.g. a mono pump or piston pump or other suitable pump, into the solid-liquid separation stage. Selection of the pump is based on e.g. feed concentration and/or viscosity of the lignocellulose material.

The solid-liquid separation stage may comprise one or more separation steps. In one embodiment, the solid-liquid separation is carried out in one or more separation steps in the separation stage. In one embodiment, the solid-liquid separation stage comprises more than one sequential separation steps. In one embodiment, the solid-liquid separation stage comprises different procedures which may be done in separate separation steps. Alternatively, more than one procedure is done in one process step.

In one embodiment, the separation of the soluble carbohydrate containing fraction and the washing filtrate is carried out in the same separation step. In one embodiment, the separation of the soluble carbohydrate containing fraction and the washing filtrate is carried out in the separate separation steps. In one embodiment, the soluble carbohydrate containing fraction is separated in one step. In one embodiment, the soluble carbohydrate containing fraction may be separated at the first step in two-step process or multistep process. In one embodiment, the soluble carbohydrate containing fraction may be separated at the last step in two-step process or multi-step process. In one embodiment, the soluble carbohydrate containing fraction may be separated between the first and the last steps. Alternatively, the soluble carbohydrate containing fraction may be separated in more than one step. In one embodiment, a part of the soluble carbohydrates or a part of the soluble carbohydrate containing fraction may be separated in connection with the pretreatment process in which the lignocellulose material is formed and/or treated. In one embodiment, the washing filtrate is separated in one step. In one embodiment, the washing filtrate is separated in more than one step. In one embodiment, the soluble carbohydrate containing fraction and/or washing filtrate is separated in each separation step.

In one embodiment, a washing filtrate is not separated from lignocellulose material (3). Then, only a soluble carbohydrate containing fraction (10) is separated from lignocellulose material (3). In one embodiment, a washing step is not carried out, and the washing filtrate is not formed. Then, only a soluble carbohydrate containing fraction (10) is separated from lignocellulose material (3).

In one embodiment, the method comprises more than one separation stages. In one embodiment, the method comprises more than one sequential separation stages.

In one embodiment, the apparatus comprises more than one separation devices. In one embodiment, the solid-liquid separation stage comprises at least one separation device. In one embodiment, the solid-liquid separation stage comprises more than one separation device. In one embodiment, one or more separation steps can be done in the same separation device. In one embodiment, the separation device comprises one or more separation step, e.g. separation segment.

In one embodiment, the separation device is based on a countercurrent washing. In one embodiment, the separation device is selected from the group consisting of filtration device, centrifugal device and their combinations. In one embodiment, the separation device is selected from the group consisting of pressure filtration device, vacuum filtration device, filtration device based on underpressure, filtration device based on overpressure, filter press, other suitable press, centrifugal device and their combinations. In one embodiment, the separation device is a pressure filtration device, vacuum filtration device, filtration device based on underpressure or filtration device based on overpressure. Alternatively, the separation device can be another washing device in which low amount of washing water is used and washing is done in high dry matter content. Then good recovery can be achieved.

Preferably, the solid-liquid separation stage comprises the separation of the soluble carbohydrate containing fraction and/or the washing filtrate from lignocellulose material. In one embodiment, the soluble carbohydrate containing fraction and/or the washing filtrate are separated from lignocellulose material by means of filtration, centrifugal treatment or their combinations. In one embodiment, the filtration is carried out by pressure, underpressure or overpressure.

In one embodiment, the solid-liquid separation stage comprises a filtration in which the soluble carbohydrate containing fraction is separated in a liquid form and a solid cake is formed. Preferably, pressure is used in the filtration. In one embodiment, liquid is separated by a pressure difference, such as by means of vacuum or overpressure. In one embodiment, the solid-liquid separation stage comprises a washing in which a displacement washing of the lignocellulose material is carried out with small amount clean water in order to remove majority of sugars, inhibitors and other soluble compounds from the solid lignocellulose material and to provide high recovery of soluble compounds. Preferably, ratio of washing water to solid is below 6, preferably below 3 and more preferably below 1.5. In one embodiment, the solid-liquid separation stage comprises the filtration and washing. In one embodiment, the filtration and washing is carried out in a static chamber, preferably in a non-moving chamber. In one embodiment, the filtration and washing is carried out in one device under pressure without mixing between the filtration and washing. Preferably, said separation device comprising the filtration and washing is in the vertical or horizontal plane, not in the inclined plane. High concentration and recovery of soluble material in the liquid phase can be achieved with small amount of clean water, and a solid fraction without soluble compounds can be achieved.

In one embodiment, the separation stage comprises the extraction, liquid separation and washing.

In one embodiment, the soluble carbohydrate containing fraction and/or the washing filtrate are separated from lignocellulose material by means of pressure filtration. In one embodiment, the apparatus comprises at least one pressure filtration device as the solid-liquid separation device. In one embodiment, the solid-liquid separation stage comprises one pressure filtration device. In one embodiment, the solid-liquid separation stage comprises more than one pressure filtration device. In a preferred embodiment, the washing in the pressure filtration device is based on a displacement of liquid. In one embodiment, the pressure filtration comprises a pumping step, pressing, washing step, pressing and removal of a cake. In the pumping step, the solid cake is formed and pressed. Preferably, in the pumping step, a chamber of the pressure filtration device is filled, and pre-pressing is made. In one embodiment, air blow is made after the pumping step or after the first pressing step to further remove liquid from the cake. Preferably, the soluble carbohydrate containing fraction is separated in connection with the pumping step. In the washing step, washing water is pressed through the cake and the cake is pressed and preferably dewatered. In the washing step, the liquid of the cake can be displaced by water. In one embodiment, air blow is made in the washing step to further remove liquid from the cake. The washing filtrate is separated by pressing in connection with the washing step. The dewatered solid cake is removed from the pressure filtrate device. Preferably, the dewatered solid cake forms a solid fraction. An advantage of the pressure filtration is that all separation steps can be carried out by one device.

In different separation stages the separation can be carried out by means of similar or different separation methods or separation devices.

In one embodiment, an amount of the washing filtrate is optimized by adjusting washing water ratio. In one embodiment, the ratio of the washing water to solid composition is 1:1-6:1, preferably, 1:1-5:1, more preferable 1:1-4:1, most preferable 1:1-3:1, in the washing. Preferably, the water balance is optimized in the method of the present invention.

In one embodiment, at least a part of the washing filtrate and/or soluble carbohydrate containing fraction is recirculated to the lignocellulose material before the separation stage. In one embodiment, at least a part of the washing filtrate and/or soluble carbohydrate containing fraction is recirculated to the lignocellulose material before the desired separation step of the separation stage, e.g. before the first separation step or between two separation steps. In one embodiment, at least a part of the washing filtrate and/or soluble carbohydrate containing fraction is recirculated back to the lignocellulose material which is fed in the same separation stage. In one embodiment, at least a part of the washing filtrate and/or soluble carbohydrate containing fraction is recirculated to the lignocellulose material which is fed to the next separation stage or next separation step of the separation stage. In one embodiment, at least a part of the washing filtrate and/or soluble carbohydrate containing fraction is recirculated by supplying into a blow tank, into entry side of solid-liquid separation device, into entry side of feeding device or into first step of the solid-liquid separation device, e.g. into first step of the pressure filtration device. In one embodiment, at least a part of the washing filtrate and/or soluble carbohydrate containing fraction is recirculated back to a desired separation step, e.g. segment, of the separation device. In one embodiment, at least a part of the washing filtrate and/or soluble carbohydrate containing fraction is recirculated back to a previous separation step, e.g. segment, of the separation device. In one embodiment, at least a part of the washing filtrate and/or soluble carbohydrate containing fraction is recirculated back to a previous separation step, e.g. segment, from each separation step in the separation device. In one embodiment, at least a part of the washing filtrate and/or soluble carbohydrate containing fraction is recirculated continuously. In one embodiment, at least a part of the washing filtrate and/or soluble carbohydrate containing fraction is recirculated in each separation step of the separation stage or in each separation stage. An amount of washing water can be decreased by means of the recirculation.

In one embodiment, the washing filtrate is recirculated, preferably totally, to the lignocellulose material. In one embodiment, 80-100 w-% of the washing filtrate is recirculated to the lignocellulose material. In one embodiment, the washing filtrate contains washing water and carbohydrates, such as galactose, glucose, mannose, arabinose, xylose, glucuronic acid and galacturonic acid. Further, the washing filtrate may contain soluble lignin.

In one embodiment, at least a part of the soluble carbohydrate containing fraction is recirculated to lignocellulose material. In one embodiment below 80 w-%, in one embodiment below 50 w-%, in one embodiment below 30 w-%, and in one embodiment below 20 w-%, of the soluble carbohydrate containing fraction of all liquid with soluble carbohydrates and other compounds is recirculated to the lignocellulose material.

In one embodiment, recirculation rate of the soluble carbohydrate containing fraction without the washing filtrate can be 0-95%, more preferably 60 90%, in one step process. When the washing filtrate is also used as dilution water recirculation rate of the soluble carbohydrate containing fraction can be 0-90%, more preferably 35-80%, in one step process.

In one embodiment, at least a part of the soluble carbohydrate containing fraction is recirculated to lignocellulose material. In one embodiment, the washing filtrate is recirculated to lignocellulose material. In one embodiment, a mixture of the washing filtrate and soluble carbohydrate containing fraction is recirculated to the lignocellulose material. In one embodiment, the washing filtrate and soluble carbohydrate containing fraction is mixed to form a mixture, and the mixture is recirculated to the lignocellulose material.

Preferably, the feed concentration of the lignocellulose material is optimized by recirculation composition.

In one embodiment, the sugar concentrate of the soluble carbohydrate containing fraction is optimized. Preferably, the soluble carbohydrate containing fraction contains soluble C5 carbohydrates. Total carbohydrate content can be measured with HPLC after acid hydrolysis according to standard SCAN-CM 71:09. Monomeric carbohydrate content can be measured with HPLC from liquid fraction directly without acid hydrolysis. The soluble carbohydrate containing fraction may contain also C6 carbohydrates, preferably below 20 w-%. Preferably, the soluble carbohydrate containing fraction can contain other monosaccharides, disaccharides, oligosaccharides and/or polysaccharides. In one embodiment, the soluble carbohydrate containing fraction contains galactose, glucose, mannose, arabinose, xylose, glucuronic acid and galacturonic acid. In one embodiment, the soluble carbohydrate containing fraction comprises soluble C5 carbohydrates, such as $C_5H_{10}O_5$ or $C_5(H_2O)_n$, and other carbohydrates and some other compounds. In one embodiment, the soluble carbohydrate concentrate of the soluble carbohydrate containing fraction is over 50 g/l, preferably over 70 g/l, more preferable over 100 g/l after the solid-liquid separation. In one embodiment, the soluble carbohydrate concentrate of the soluble carbohydrate containing fraction is below 250 g/l, in one embodiment below 200 g/l, in one embodiment below 150 g/l after the solid-liquid separation. In one embodiment, the soluble carbohydrate concentrate of the soluble carbohydrate containing fraction is between 15 to 280 g/l, preferably 30 to 200 g/l, more preferable 50 to 165 g/l after the solid-liquid separation. Preferably, the soluble carbohydrate containing fraction is in the form of solution. In one embodiment, water soluble matter is between 20 to 425 g/l, preferably 45 to 303 g/l, more preferable 75 to 250 g/l after the solid-liquid separation. Water soluble matter can be determined by means of a method described later as "gravimetric washing method".

Preferably, at least a part of the soluble carbohydrate containing fraction is supplied out from the separation stage. The soluble carbohydrate containing fraction can be supplied out after any desired step of the separation stage. In one embodiment, the soluble carbohydrate containing fraction is supplied out after the first step of the separation stage.

In one embodiment a soluble carbohydrate containing fraction (10) with high concentration can be formed. The soluble carbohydrate containing fraction is formed from lignocellulose material (3) which has been formed by treating plant based raw material (1), wherein the soluble carbohydrate containing fraction has been formed by separating the soluble carbohydrate containing fraction (10) and/or a washing filtrate (12) from solid lignocellulose material (3) in one or more separation stage (4,6) and by recirculating at least a part of the soluble carbohydrate containing fraction and/or washing filtrate to the lignocellulose material for increasing concentration of the soluble carbohydrate containing fraction. The soluble carbohydrate containing fraction may be used as component in manufacturing a final product.

In one embodiment, a part of the soluble carbohydrate containing fraction (14) is separated from the lignocelluloses material (3) in connection with the pretreatment step (2,5) in which the lignocellulose material is formed and/or treated. The soluble carbohydrate containing fraction (14) may be separated by means of a similar separation method or device as used in the separation stage (4,6) or by means of other suitable separation method or device.

In one embodiment, two soluble carbohydrate containing fractions (10,14) with high concentration can be formed with high soluble compound recovery. Two soluble carbohydrate containing fractions are formed from lignocellulose material (3) which is formed by treating plant based raw material (1) in two or more steps. The first soluble carbohydrate containing fraction (14) is formed by separating a part of soluble compounds between the first and the last pretreatment steps (2,5) and the second soluble carbohydrate containing fraction (10) is formed by separating most of the soluble compounds after the last pretreatment step. Preferably, the second soluble carbohydrate containing fraction (10) is separated in the separation stage (4) so that the soluble carbohydrate containing fraction and/or a washing filtrate is separated from solid lignocellulose material and at least a part of the soluble carbohydrate containing fraction and/or washing filtrate is recirculated to the lignocellulose material for increasing concentration of the soluble carbohydrate containing fraction. The soluble carbohydrate containing fractions (14) and (10) may be combined or used separately as component in manufacturing a final product. The combined or separate soluble carbohydrate containing fractions can be concentrated for further use.

In one embodiment, two soluble carbohydrate containing fractions (10,14) with high concentration can be formed with high soluble compound recovery. Two soluble carbohydrate containing fractions are formed from lignocellulose material (3) which is formed by treating plant based raw material (1) in two or more steps. The first soluble carbohydrate containing fraction (14) is formed so that liquid-solid ratio (w/w) of the lignocellulose material is below 5:1, preferably below 4:1, more preferably below 3:1 and most preferably below 2:1 before separating a part of soluble compounds between the first and the last pretreatment steps (2,5). The second soluble carbohydrate containing fraction (10) is formed by separating most of the soluble compounds after the last pretreatment step. Preferably, the second soluble carbohydrate containing fraction (10) is separated in the separation stage (4) so that the soluble carbohydrate containing fraction and/or a washing filtrate is separated from solid lignocellulose material and at least a part of the soluble carbohydrate containing fraction and/or washing filtrate is recirculated to the lignocellulose material for increasing concentration of the soluble carbohydrate containing fraction. Fresh washing water amount is less than 4:1 (liquid:solid (w/w)), preferably less than 3:1, more preferably less than 2:1, the most preferably close to 1:1. The efficiency of removing soluble carbohydrate containing fraction from solid need to be high and it need to be higher than 60%, preferably more than 70%, more preferably more than 80%, the most preferable more than 90%. The soluble carbohydrate containing fractions (10 and (14) may be combined or used separately as component in manufacturing a final product. The combined or separate soluble carbohydrate containing fractions can be concentrated for further use.

In one embodiment, a soluble carbohydrate containing fraction (10) with high concentration can be formed with high soluble compound recovery. The soluble carbohydrate containing fraction is formed from lignocellulose material (3) which is formed by treating plant based raw material (1) in one or more steps. The soluble carbohydrate containing fraction is formed by separating most of the soluble compounds after the last pretreatment step (2,5) so that the soluble carbohydrate containing fraction and/or a washing filtrate is separated from solid lignocellulose material and at least a part of the soluble carbohydrate containing fraction and/or washing filtrate is recirculated to the lignocellulose material for increasing concentration of the soluble carbohydrate containing fraction. The soluble carbohydrate containing fraction may be used as component in manufacturing a final product. The soluble carbohydrate containing fractions can be concentrated for further use.

In one embodiment, a soluble carbohydrate containing fraction (10) with high concentration can be formed with high soluble compound recovery. The soluble carbohydrate containing fraction is formed from lignocellulose material (3) which is formed by treating plant based raw material (1) in one or more steps. The soluble carbohydrate containing fraction is formed by separating most of the soluble compounds after the the last pretreatment step (2,5) so that the soluble carbohydrate containing fraction and/or a washing filtrate is separated from solid lignocellulose material and at least a part of the soluble carbohydrate containing fraction and/or washing filtrate is recirculated to the lignocellulose material for increasing concentration of the soluble carbohydrate containing fraction. Fresh washing water amount is less than 4:1 (liquid:solid(w/w)), preferably less than 3:1, more preferably less than 2:1, the most preferably close to 1:1. The efficiency of removing soluble carbohydrate containing fraction from solid need to be high and it need to be higher than 70%, preferably more than 80%, more preferably more than 90%, the most preferable more than 95%. The soluble carbohydrate containing fraction may be used as component in manufacturing a final product. The soluble carbohydrate containing fractions can be concentrated for further use.

In one embodiment, the soluble carbohydrate containing fraction is recovered. In one embodiment, the soluble carbohydrate containing fraction is supplied to a further processing. In one embodiment, the monomerization of the soluble carbohydrate containing fraction is made before the further processing. In one embodiment, the soluble carbohydrate containing fraction is supplied to a fermentation process. In one embodiment, the soluble carbohydrate containing fraction is used as a source material in fermentation. In one embodiment, the soluble carbohydrate containing fraction is supplied to a hydrolysis process. In one embodiment, the soluble carbohydrate containing fraction is used as a source material in hydrolysis, such as by acid hydrolysis, enzymatic hydrolysis or the like. In one embodiment, the soluble carbohydrate containing fraction is supplied to a catalytic treatment process. In one embodiment, the soluble carbohydrate containing fraction is used as a source material in the catalytic process. The soluble carbohydrate containing fraction may be supplied directly to a fermentation, hydrolysis, catalytic treatment process or other suitable process, or alternatively via a suitable treatment step or an additional step, e.g. additional concentration step or purification step, to a fermentation, hydrolysis, catalytic treatment process or other suitable process.

In one embodiment, at least a part of the washing filtrate is supplied to another process or process step. In one embodiment, the washing filtrate is used as a dilution water in the other process, e.g. in the pretreatment process. In one embodiment, the washing filtrate is used as a washing water in the other process.

Solids (11) are supplied out from the solid-liquid separation stage (4,6). In one embodiment, a solid fraction comprising solids is supplied out from the solid-liquid separation stage. In one embodiment, the solid fraction comprising solids (11) is formed from lignocellulose material (3) which has been formed by treating plant based raw material (1) so that the solid fraction has been formed by separating a soluble carbohydrate containing fraction (10) and/or a washing filtrate (12) from solid lignocellulose material by means of at least one solid-liquid separation stage (4,6) and by recirculating at least a part of the soluble carbohydrate containing fraction and/or the washing filtrate to the lignocellulose material (3), and the solids (11) has been recovered from the separation stage. In one embodiment, the solids comprises C6 carbohydrates, such as ($C_6CH_{12}O_6$ or ($C_6(H_2O)_n$), other solid carbohydrates and lignin, and some other compounds, such as some residual soluble material. In one embodiment, the solid fraction is in the form of a cake. In one embodiment, dry matter content of the cake is 40-80% by weight, preferably 45-70% by weight, more preferably 50-60% by weight, after the solid-liquid separation stage. In one embodiment, dry matter content of the cake is 7-70% by weight, preferably 15-45% by weight, more preferably 25-35% by weight, after the solid-liquid separation stage. In one embodiment, the solid fraction contains soluble compounds below 15%, preferably below 6%, more preferably below 3% by weight, after the solid-liquid separation stage. In one embodiment, water soluble matter is determined by a gravimetric washing method. The determination by the gravimetric washing method may be done as following: dry matter content (DM %) of raw material, e.g. the solid and soluble fraction, is measured at 60° C., the amount of solids remaining after heating the sample at 60° C. to constant weight is measured and dry matter content is calculated based on wet and dry weights. For washing about 10 g bone dry of the wet material under investigation is taken, weighted (exact weighed amount) and mixed with hot water (50° C.) in a vessel so that total amount is 200 g, the mixture is mixed 20 s (Bamix Mono freehand food blender, 'C' blade, speed 1 (7000 rpm)), the mixture is soaked with soaking time 5 min, the mixture is mixed 10 s (Bamix Mono freehand food blender, C' blade, speed 1 (7000 rpm)), mass of a dry filter paper is measured, the mixture is filtered by means of Buchner (dia.125 mm) and the filter paper, an inward relief valve is closed when a cake is matt (dry) in whole, a filtrate is taken and the blender and vessel is washed with the filtrate and the filtrate is filtered again through the cake, the cake is washed three times with hot water, a 100 g, so that suction effect is maintained the whole time and washing water (100 g) is added when the cake is matt (dry) in whole, a foil dish is weighed, the cake with the filter paper is dried in the foil dish, the dried cake (60° C.) with the filter paper is weighed in the foil dish and mass of the filter paper and foil dish is subtracted from mass of the dried cake, filter paper and foil dish, and then soluble matter free solid, i.e. water insoluble solids (WIS) of wet material under investigation, can be determined. Water insoluble solids, WIS %, can be calculated: WIS %=(weight of washed and dried material, e.g. the cake)/(weight of the wet slurry for washing, e.g. the raw material). Water soluble matter, WS %, of dry matter can be calculated: WS %=(dry matter (DM %) of the original slurry, e.g. the raw material)–(water insoluble solids, WIS %). In one embodiment, with high soluble material content (25-50% of total dry matter soluble) of raw material, the solid fraction contains soluble compounds below 15%, preferably below 9%, more preferably below 5% by weight, after the solid-liquid separation stage, measured by gravimetric washing method. In one embodiment, with lower soluble material content (below 25% of total dry matter soluble) of raw material, the solid fraction contains soluble compounds below 9%, preferably below 6%, more preferably below 3% by weight, after the solid-liquid separation stage, measured by gravimetric washing method.

Particle size of the solid particles can be defined, e.g. by an optical measurement device, such as Metso FS5, or by a laser diffraction method, such as Coulter LS230. In one embodiment, particle size of the solid particles can be defined based on ISO 16065-N or TAPPI T271. Fibre length of the solid particles can be defined based on ISO 16065-N, when fibres are defined as material longer than 0.2 mm. Fibre length of the solid particles can be defined based on TAPPI T271, when fibre length is 0.01 to 7.60 mm. In connection with Metso FS5, Lc means contour length, i.e. centerline fiber length, which is fiber length measured from the fibers center line from one end to another. Length-weighted Lc(l) means length-weighted fiber length which is average fiber length measured from a fiber distribution weighted according to the TAPPI T271 standards. Weight-weighted Lc(w) means weight-weighted fiber length which is likewise average fiber length measured from a fiber distribution weighted according to the TAPPI T271 standards. Arithmetic Lc(n) means arithmetic mean which is calculated from the population distribution of fibers. In this result average length is calculated from the length distribution. F1(l) % means length weighted distribution % (width>10 µm, length<0.2 mm). Fiber width is measured as integral value from the middle of the fiber to account for tapered ends.

In one embodiment, length-weighted particle length Lc(l) is below [(0.4)×(corresponding unrefined sulphate pulp fibre length)], preferably below [(0.3)×(corresponding unrefined sulphate pulp fibre length)], more preferable below [(0.2)× (corresponding unrefined sulphate pulp fibre length)], most preferable below [(0.1)×(corresponding unrefined sulphate pulp fibre length)].

In one embodiment, fine particle width (fraction 0-0.2 mm) is below [(0.7)×(corresponding unrefined sulphate pulp fibre length)], preferably below [(0.6)×(corresponding unrefined sulphate pulp fibre length)], more preferable below [(0.5)×(corresponding unrefined sulphate pulp fibre length)], most preferable below [(0.4)×(corresponding unrefined sulphate pulp fibre length)].

In one embodiment, the solid fraction comprises fine solid particles which are fiber-like or indefinable particles with longest dimension shorter than 0.2 mm measured with optical Metso FS5 (fraction F1(l) of length weighted Lc(l) measurements and calculations). In one embodiment, the solid fraction of hardwood comprises particles with longest dimension shorter than 0.2 mm over 70% (F1(l)>70%), preferably over 80%, more preferably over 90% and most preferably over 98% by weight, defined by Metso FS5. In one embodiment, the solid fraction of softwood comprises particles with longest dimension shorter than 0.2 mm over 50% (F1(l)>50%), preferably over 60%, more preferably over 70% and most preferably over 80% by weight, defined by Metso FS5.

In one embodiment, the solid fraction comprises fine solid particles which are fiber-like or indefinable particles. The length weighted length Lc(l) of solid fraction is measured based TAPPI T271 standard includes all the particles detected and filling the requirements of measurement. TAPPI T271 defines fiber length of material to have longest dimension from 0.01 to 7.60 mm.

In one embodiment, the solid fraction comprises fine solid particles which are fiber-like or indefinable particles. The length weighted length Lc(l) of solid fraction is measured with Metso FS5. The length weighted Lc(l)-value is 40% or less of the length of corresponding unrefined sulphate pulp fibre length, preferably 30% or less, more preferably 20% or less, most preferably 10% or less. And the width of the fine particle fraction of length weighted particles (Lc(l)fraction 0-0.2 mm) is 70% or less of width of the corresponding sulphate pulp fibre, preferably 60% or less, more preferably 50% or less, the most preferably 40% or less.

In one embodiment, the solid fraction of hardwood comprises fine solid particles which are fiber-like or indefinable particles. The length weighted length Lc(l) of solid fraction is measured with Metso FS5. The length weighted Lc(l) fractions over 0.2 mm fibre length is 50% or less, preferably 35% or less, more preferably 20% or less, most preferably 5% or less.

In one embodiment, the solid fraction of softwood comprises fine solid particles which are fiber-like or indefinable particles. The length weighted length Lc(l) of solid fraction is measured with Metso FS5. The length weighted Lc(l) fractions over 0.2 mm fibre length is 60% or less, preferably 45% or less, more preferably 30% or less, most preferably 15% or less.

In one embodiment, a solid fraction comprising solids (11) is supplied out from the solid-liquid separation stage (4,6,). In one embodiment, the solid fraction is supplied out after the latest solid-liquid separation stage. In one embodiment, at least a part of the solid fraction is supplied out between two separation stages or between two separation steps.

In one embodiment, the solid fraction is supplied to a hydrolysis which may be selected from the group consisting of acid hydrolysis, enzymatic hydrolysis, supercritical hydrolysis and/or subcritical hydrolysis and their combinations, or to a manufacture of a composite material or a combustion process or other suitable process or their combinations. The solid fraction may be supplied directly to a hydrolysis, manufacture of a composite material, combustion process or other suitable process, or alternatively via a suitable treatment step or an additional step, e.g. additional concentration step or purification step, to a hydrolysis, manufacture of a composite material, combustion process or other suitable process.

The method according to the present invention provides the soluble carbohydrate containing fraction and solid fraction with high concentration and with good quality. The solid fraction has very high concentration of lignin and glucan and its hydrated products. Further, the solid fraction has very high purity. In the present invention water balance can be optimized. Then the soluble carbohydrate content can be increased in the soluble carbohydrate containing fraction. The present invention demonstrates improved sugar recovery. Further, the present invention minimizes waste water, and decreases post-treating costs of the soluble carbohydrate containing fraction. High concentration is achieved with low energy consumption.

The present invention provides an industrially applicable, simple and affordable way of making the soluble carbohydrate containing fraction with high concentration. The method according to the present invention is easy and simple to realize as a production process. The method according to the present invention is suitable for use in the manufacture of the different sugar based fractions and final products from different starting materials.

EXAMPLES

The invention is described in more detail by the following examples with reference to accompanying drawings.

Example 1

In this example a soluble carbohydrate containing fraction is produced according to a process of FIG. 1.

The lignocellulose material (3) is formed from plant based raw material (1) by means of pre-treatment (2). The lignocellulose material (3) is fed into a solid-liquid separation stage (4) comprising a pressure filtration device. A soluble carbohydrate containing fraction (10) containing C5 sugars is separated from the lignocellulose material in the pumping and pressing step of the pressure filtration. A washing filtrate (12) is separated from the lignocellulose material (3) in the washing step of the pressure filtration. The washing filtrate (12) and at least a part of the soluble carbohydrate containing fraction (10) are recirculated to the lignocellulose material before the pressure filtration device. A solid cake (11) containing e.g. solids, solid carbohydrates, lignin and some soluble sugar, oligomer and polymer residual is removed from the pressure filtration device.

Example 2

In this example a soluble carbohydrate containing fraction is produced according to a process of FIG. 2.

The lignocellulose material (3) is formed from plant based raw material (1) by means of pre-treatment (2). The lignocellulose material (3) is fed into a solid-liquid separation stage (4) comprising a pressure filtration device. A soluble carbohydrate containing fraction (10) containing C5 sugars is separated from the lignocellulose material in the pumping and pressing step of the pressure filtration. A washing filtrate (12) is separated from the lignocellulose material (3) in the washing step of the pressure filtration. The washing filtrate (12) is recirculated to the lignocellulose material before the pressure filtration device. The soluble carbohydrate containing fraction (10) including C5 sugars is removed from the pressure filtration device. A solid cake (11) containing e.g. solids, solid carbohydrates, lignin and some soluble sugar, oligomer and polymer residual is removed from the pressure filtration device.

Example 3

In this example a soluble carbohydrate containing fraction is produced according to a process of FIG. 3.

The lignocellulose material (3) is formed from plant based raw material (1) by means of pre-treatment (2). The lignocellulose material (3) is fed into a solid-liquid separation stage (4) comprising a pressure filtration device. A soluble carbohydrate containing fraction (10) containing C5 sugars is separated from the lignocellulose material in the pumping and pressing step of the pressure filtration. A washing filtrate (12) is separated from the lignocellulose material in the washing step of the pressure filtration. The washing filtrate (12) may be recirculated to the pretreatment (2) of the lignocellulose material. Alternatively, the washing filtrate (12) is removed from the pressure filtration device and recirculated to other process. At least a part of the soluble carbohydrate containing fraction (10) is recirculated to the lignocellulose material before the pressure filtration device. A solid cake (11) containing e.g. solids, solid carbohydrates, lignin and some soluble sugar, oligomer and polymer residual is removed from the pressure filtration device.

Example 4

In this example a soluble carbohydrate containing fraction is produced according to a process of FIG. 4.

The lignocellulose material (3) is formed from plant based raw material (1) by means of pre-treatment (2). The lignocellulose material (3) is fed into a solid-liquid separation stage (4) comprising a filtration device. A soluble carbohydrate containing fraction (10) containing C5 sugars is separated from the lignocellulose material in the filtration. At least a part of the soluble carbohydrate containing fraction (10) is recirculated to the lignocellulose material before the filtration device. A solid cake (11) containing e.g. solids, solid carbohydrates, lignin and some soluble sugar, oligomer and polymer residual is removed from the filtration device.

Example 5

In this example a soluble carbohydrate containing fraction is produced according to a two-step process of FIG. 5.

The lignocellulose material (3) is formed from plant based raw material (1) by means of pre-treatment (2), e.g. by milling. The lignocellulose material (3) is fed into the first solid-liquid separation stage (4) comprising a pressure filtration device. A soluble carbohydrate containing fraction (10) containing C5 sugars is separated from the lignocellulose material in the pumping and pressing step of the pressure filtration. A washing filtrate (12) is separated from the lignocellulose material (3) in the washing step of the pressure filtration. The washing filtrate (12) and at least a part of the soluble carbohydrate containing fraction (10) are recirculated to the lignocellulose material before the first pressure filtration device. A part of the soluble carbohydrate containing fraction (10) may be removed from the process before the second separation step.

In the second step the lignocellulose material (3) is treated by means of treatment stage (5), e.g. by physical, chemical or physic-chemical treatment such as by microwave or ultrasound treatment, or by steam explosion. The lignocellulose material is fed into the second solid-liquid separation stage (6) comprising a pressure filtration device. A soluble carbohydrate containing fraction (10) containing C5 sugars is separated from the lignocellulose material in the pumping and pressing step of the pressure filtration. A washing filtrate (12) is separated from the lignocellulose material in the washing step of the pressure filtration. The washing filtrate (12) and at least a part of the soluble carbohydrate containing fraction (10) are recirculated to the lignocellulose material before the first and/or second pressure filtration device. At least a part of the soluble carbohydrate containing fraction (10) is removed from the process.

A solid cake (11) containing e.g. solids, solid carbohydrates, lignin and some soluble sugar, oligomer and polymer residual is removed from the pressure filtration device.

Example 6

In this example a soluble carbohydrate containing fraction is produced according to a two-step process of FIG. 6.

The lignocellulose material (3) is formed from plant based raw material (1) by means of pre-treatment (2), e.g. by milling. The lignocellulose material (3) is fed into the first solid-liquid separation stage (4) comprising a pressure filtration device. A soluble carbohydrate containing fraction (10) containing C5 sugars is separated from the lignocellulose material in the pumping and pressing step of the pressure filtration. A washing filtrate (12) is separated from the lignocellulose material (3) in the washing step of the pressure filtration. The washing filtrate (12) and at least a part of the soluble carbohydrate containing fraction (10) are recirculated to the lignocellulose material before the second separation device. A part of the soluble carbohydrate containing fraction (10) may be removed from the process before the second separation step.

In the second step the lignocellulose material (3) is treated by means of treatment stage (5), e.g. by physical, chemical or physic-chemical treatment such as by microwave or ultrasound treatment, or by steam explosion. The lignocellulose material is fed into the second solid-liquid separation stage (6) comprising a pressure filtration device. A soluble carbohydrate containing fraction (10) containing C5 sugars is separated from the lignocellulose material in the pumping and pressing step of the pressure filtration. A washing filtrate (12) is separated from the lignocellulose material in the washing step of the pressure filtration. The washing filtrate (12) and at least a part of the soluble carbohydrate containing fraction (10) are recirculated to the lignocellulose material before the second pressure filtration device. At least a part of the soluble carbohydrate containing fraction (10) is removed from the process.

A solid cake (11) containing e.g. solids, solid carbohydrates, lignin and some soluble sugar, oligomer and polymer residual is removed from the pressure filtration device.

Example 7

In this example a soluble carbohydrate containing fraction is produced according to a process of FIG. 7.

The lignocellulose material (3) is formed from plant based raw material (1) by means of the first pretreatment (2), e.g. by hydrolysis. After the pretreatment a part of the soluble carbohydrates (14) is separated (13) in connection with the first pretreatment step (2). The lignocellulose material (3) is fed into the second pre-treatment step (5) in which the lignocelluloses material is treated, e.g. by steam explosion. After that the lignocellulose material (3) is fed into a solid-liquid separation stage (4) comprising a pressure filtration device. A soluble carbohydrate containing fraction (10) containing C5 sugars is separated from the lignocellulose material in the pumping and pressing step of the pressure filtration. A washing filtrate (12) is separated from the lignocellulose material (3) in the washing step of the pressure filtration. The washing filtrate (12) and at least a part of the soluble carbohydrate containing fraction (10) are recirculated to the lignocellulose material before the pressure filtration device. A solid cake (11) containing e.g. solids, solid carbohydrates, lignin and some soluble sugar, oligomer and polymer residual is removed from the pressure filtration device. At least a part of the soluble carbohydrate containing fractions (10,14) is removed from the process.

Example 8

In this example a soluble carbohydrate containing fraction is produced.

Birch wood chips were pretreated in one-step autohydrolysis and steam explosion process to dissolve hemicellulose. The formed pretreated lignocellulose material was mixed with hot water and stirred for few hours. Then solid-liquid separation was done with Outotec Larox FP 0.3 two way pressure filter as described in the table 1. Filtration area was 0.27 m². To simulate the increase of concentration the soluble carbohydrate containing filtrate (10) of first pressing was used as a dilution water of next round, and again after second filtration the soluble carbohydrate containing filtrate of pressing was used in dilution of third filtration. Finally 5 filtration rounds were done. Filtration conditions are shown in Table 1.

TABLE 1

| Washing with filter press | | | |
|---|---|---|---|
| Target dry matter content of pretreated lignocellulose material for filter press | % | | 12 |
| Dry matter content of pretreated raw material | % | | 65 |
| Temperature of pretreated lignocellulose material for filter press | ° C. | | 45-60 |
| Feeding and first press | | | |
| Feeding time | min | | 3-6 |
| Pressure in feeding | bar | | 3-5 |

TABLE 1-continued

| Pressing pressure | bar | 5-6 |
|---|---|---|
| Pressing time | min | 2 |
| Washing conditions | | |
| Wash water temperature | ° C. | 40-60 |
| Pressing pressure | bar | 10 |
| Pressing time | min | 2 |
| Air blowing | | |
| Blowing time | min | 1 |
| Air flow | l/min | 150-250 |

Figure 8:
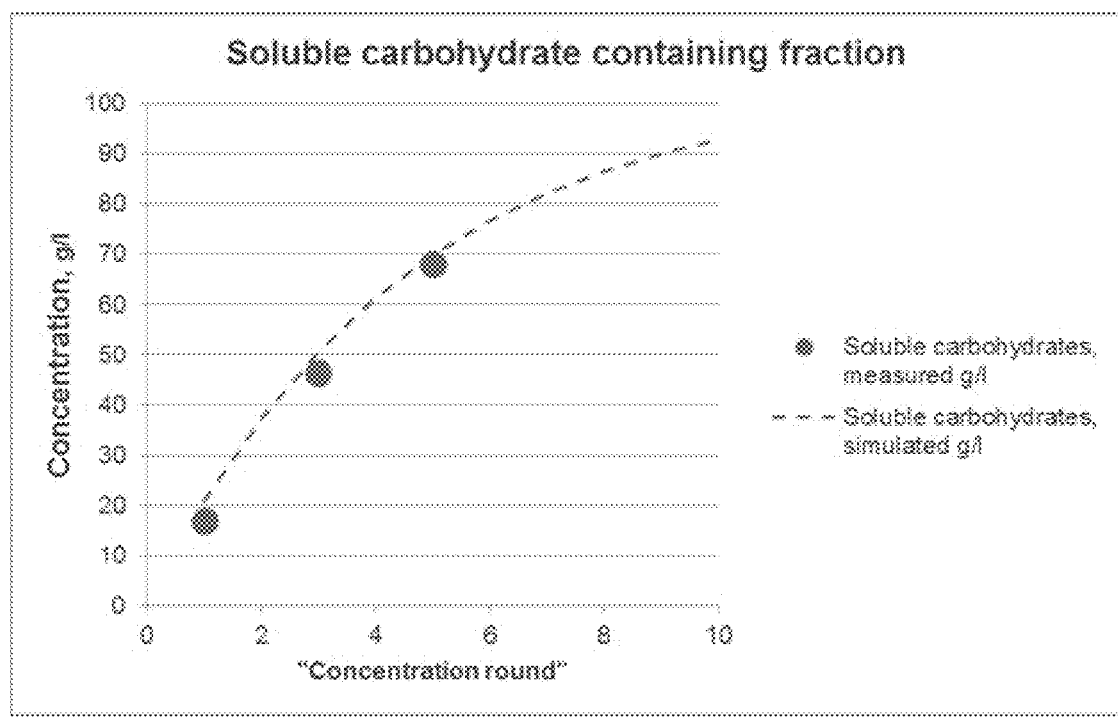
FIG. 8 shows results from one example carried out according to one method embodiment of the present invention.

Total carbohydrate content was measured based on SCAN-CM 71 standard: acid hydrolysis and HPLC was used. As seen in FIG. 8, the carbohydrate content is increasing very well in line with simulated concentration curve.

Figure 9:
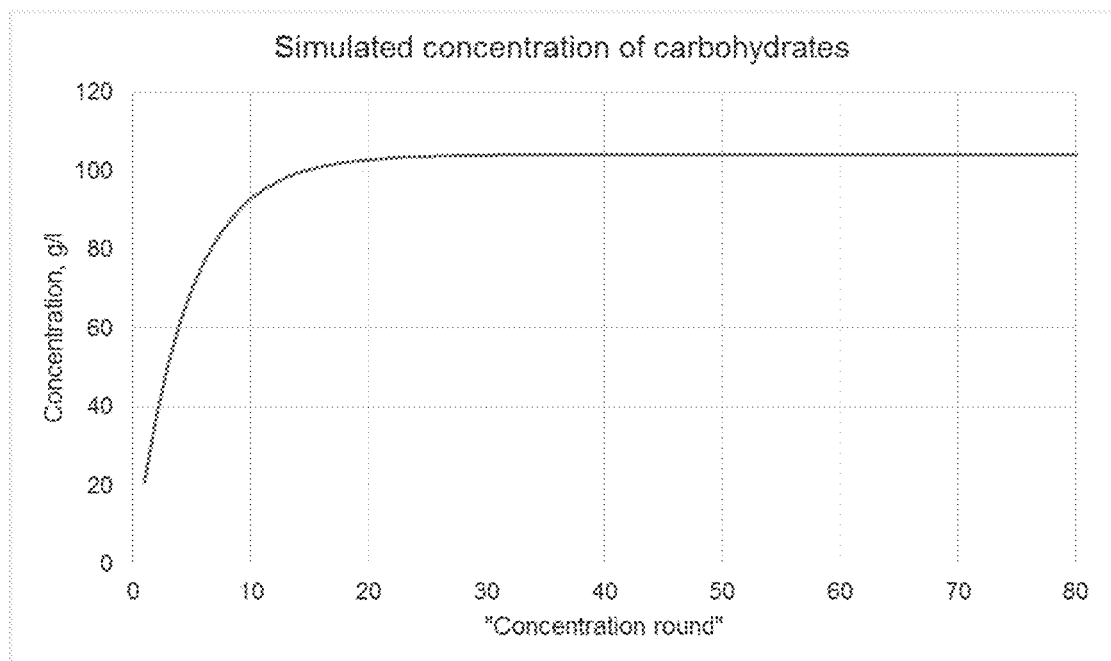
FIG. 9 shows results from one example carried out according to one method embodiment of the present invention.

Simulation of the example was done with assumption of 15.7% dissolving carbohydrate content of the pretreated lignocellulose material, which was also measured value of the lignocellulose material in example 8. As seen in FIG. 9, the concentration of the soluble carbohydrate containing filtrate coming out of the process will reach level of 104 g/l in continuous process.

Example 9

In this example a soluble carbohydrate containing fraction is produced.

Birch wood chips were pretreated in one-step autohydrolysis and steam explosion process to dissolve hemicellulose. The formed lignocellulose material was mixed with hot water and stirred for few hours. Then solid-liquid separation was done with Outotec Larox FP 0.3 two way pressure filter as described in the table 1. Filtration area was 0.27 m². Amount of washing water was 2:1 (water:water insoluble solids).

Figure 10:
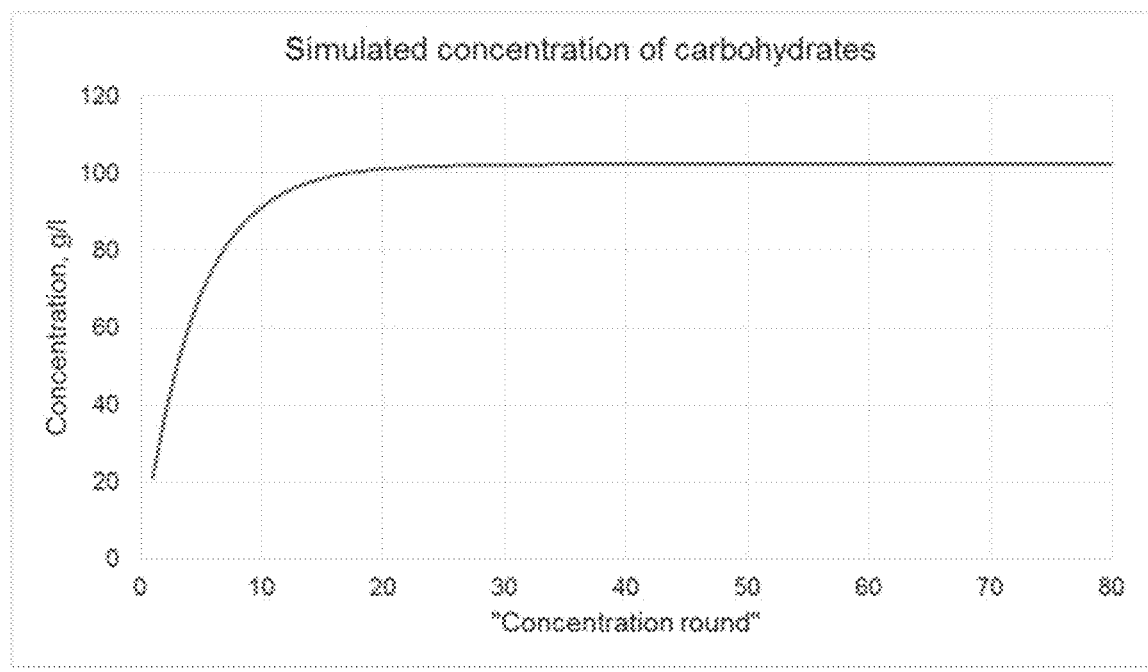
FIG. 10 shows results from one example carried out according to one method embodiment of the present invention.

To simulate the increase of concentration when all the washing filtrate (12) of the process and some soluble carbohydrate containing filtrate (10) of first pressing was calculated to use as dilution water of next round, and again after second filtration the washing filtrate and some soluble carbohydrate containing filtrate of pressing was used in dilution of third filtration. In this case about 77% of dilution liquid was soluble carbohydrate containing filtrate. Recirculated soluble carbohydrate containing fraction was 70% of all liquid with soluble compounds. Washing efficiency was assumed to be 90%. Finally more than 70 iteration rounds were done. Simulation of the example was done with assumption of 15.7% dissolving carbohydrate content of the pretreated lignocellulose material, which was also measured value of the lignocellulose material in example 8. As seen in FIG. 10, the concentration of soluble carbohydrate containing filtrate coming out of the process will reach level of 102 g/l in continuous process.

Example 10

In this example a liquid and solid fraction is produced.

Birch wood chips were pretreated in two-step dilute acid steam explosion process to dissolve hemicellulose and to create soluble carbohydrate containing fraction. Portion of this soluble carbohydrate containing fraction is removed before rapid pressure release of lignocellulose material in the steam explosion. The formed lignocellulose material was mixed with hot water and stirred for a while. Then solid-liquid separation was done with Outotec Larox PF 0.1 pressure filter as described in the Table 2. Filtration area was 0.1 m². Amount of washing water was 1:1 (water:dry matter in the cake) and 3:1. Results are shown in Table 3. Water soluble matter of dry matter is measured with gravimetric washing method.

TABLE 2

Washing with pressure filter

| | | |
|---|---|---|
| Target dry matter content of pretreated lignocellulose material for filter press | % | 16 |
| Dry matter content of pretreated raw material | % | 27 |
| Temperature of pretreated lignocellulose material for filter press | ° C. | 60 |
| Feeding and first press | | |
| Feeding time | min | 2.0 |
| Pressure in feeding | bar | 5.0 |
| Pressing pressure 1 | bar | 5-6 |
| Pressing time | min | 2 |
| Washing conditions | | |
| Wash water temperature | ° C. | 65 |
| Pressing pressure | bar | 16 |
| Pressing time | min | 3.5 |
| Air blowing | | |
| Blowing time | min | 1.5 |
| Air flow | l/min | <50 |

TABLE 3

| Pressure filtration with PF 0.1 | Lignocellulose material | Only pressing | Pressing + washing 1:1 | Pressing + washing 3:1 |
|---|---|---|---|---|
| Dry matter, % | 18.6 | | | |
| Water insoluble solids, % | 15.1 | 47.3 | 47.6 | 49.1 |
| Water soluble matter of dry matter, % | 18.4 | 5.4 | 3.2 | 2.3 |

Example 11

In this example a liquid and solid fraction is produced.

Birch wood chips were pretreated in two-step dilute acid steam explosion process to dissolve hemicellulose. The formed lignocellulose material was mixed with hot water and stirred for a while. Then solid-liquid separation was done with vacuum filtration filter as described in the Table 4 (Vacuum filtration in laboratory). Filtration area was 0.1 m². Amount of washing water varied from 0 to 8.6 (water:dry matter in the cake).

TABLE 4

| Vacuum filtration with Büchner | | Test 1 | Test 2 | Test 3 | Test 4 |
|---|---|---|---|---|---|
| Dry matter content of pretreated lignocellulose material for vacuum filter | % | 19 | 19 | 19 | 19 |
| Water insoluble solids of slurry | % | 15 | 15 | 15 | 15 |
| Temperature of slurry | ° C. | 50 | 60 | 60 | 60 |
| Fed slurry | ml | 500 | 500 | 500 | 500 |
| Vacuum | mbar | 0.6 | 0.6 | 0.6 | 0.6 |

TABLE 4-continued

| Vacuum filtration with Büchner | | Test 1 | Test 2 | Test 3 | Test 4 |
|---|---|---|---|---|---|
| Drying time | s | 60 | 10 | 10 | 10 |
| Temperature of washing water | ° C. | | 60 | 60 | 60 |
| Amount of washing water | l | | 250 | 500 | 750 |
| Washing liquid/solid | | 0 | 2.7 | 5.7 | 8.6 |
| Drying time | min | 0 | 60 | 60 | 60 |
| Air flow | l/min | 35 | 35 | 35 | 35 |
| Cake wet thickness | mm | 24 | 26 | 28 | 26 |
| Dry matter of cake | % | 32.9 | 31.4 | 30.4 | 30.8 |
| Water soluble matter of dry matter | % | 18.4 | 9.2 | 5.9 | 3.2 |

Example 12

In this example a concentrated liquid and purified solid fraction is produced, based on example 10.

Birch wood chips were pretreated in two-step dilute acid steam explosion process to dissolve hemicellulose. The formed lignocellulose material was mixed with hot water and stirred for a while. Then solid-liquid separation was done with Outotec Larox PF 0.1 pressure filter as described in the Table 2. Filtration area was 0.1 m². Amount of washing water was 1:1 (water:water insoluble solids in the cake) and 3:1. Dry matter of original pretreated biomass was 65%, dry matter in the first filtration was 16%, and water insoluble solid content was 13%. Water insoluble solid content was kept constant in filter press while dry matter of slurry was increased due to increased soluble material in slurry. Dry matter of washed cake was about 50%. Composition of the solid fraction, which is further washed in laboratory like in gravimetric washing method to remove all water soluble material, is presented in Table 5. The solid fraction was washed with water in order to remove residue soluble compounds, and after that the properties were determined.

To simulate the increase of concentration when all the washing filtrate (12) of the process and some soluble carbohydrate containing filtrate (10) of first pressing was calculated to use as dilution water of next round, and again after second filtration the washing filtrate and some soluble carbohydrate containing filtrate of pressing was used in dilution of third filtration. In 1:1 washing case about 83% of dilution liquid was soluble carbohydrate containing filtrate and in 3:1 case 48% of dilution liquid was soluble carbohydrate containing filtrate. Washing efficiency was calculated to be 83% (1:1) and 88% (3:1). Finally more than 70 iteration rounds were done. Simulation of the example was done with measured soluble matter content of 18.4% of the pretreated lignocellulose material. The concentration of soluble matter containing filtrate coming out of the process will reach level of 135 g/l in continuous process with 1:1 washing and 99 g/l with 3:1 washing.

TABLE 5

| Property | Unit | Method | Test 1 | Test 2 |
|---|---|---|---|---|
| Acid-insoluble lignin, grav. | % | T-222 | 33.4 | 34.0 |
| Acid-soluble lignin, UV 205 | % | T-UM 250 | 1.5 | 1.5 |
| Arabinose, acid hydrolysis, HPAE-PAD | mg/g | SCAN-CM71 | 0.0 | 0.0 |
| Rhamnose, acid hydrolysis, HPAE-PAD | mg/g | SCAN-CM71 | 0.0 | 0.0 |
| Galactose, acid hydrolysis, HPAE-PAD | mg/g | SCAN-CM71 | 0.0 | 0.0 |
| Glucose, acid hydrolysis, HPAE-PAD | mg/g | SCAN-CM71 | 599.3 | 642.7 |
| Xylose, acid hydrolysis, HPAE-PAD | mg/g | SCAN-CM71 | 25.8 | 26.1 |
| Mannose, acid hydrolysis, HPAE-PAD | mg/g | SCAN-CM71 | 0.0 | 0.0 |
| Carbohyrates, acid hydrolysis, HPAE-PAD, total | mg/g | SCAN-CM71 | 625.1 | 668.7 |
| FS5 Length weighted fiber length Lc(l) ISO | mm | Determined | 0.310 | 0.405 |
| FS5 Fiber width | μm | by Metso | 23.8 | 19.1 |
| FS5 Fines | % | FS5 | 99.5 | 99.1 |
| FS5 Fines (Flakes) | % | based on | 95.0 | 93.5 |
| FS5 Fines (Fibrils) | % | ISO 16065-N | 0.0 | 0.0 |
| Population based particle length Lc(n) | mm | or TAPPI | 0.018 | 0.018 |
| Length weighted particle length Lc(l) | mm | T271 | 0.026 | 0.029 |
| Weight weighted particle length Lc(w) | mm | | 0.061 | 0.111 |
| FS5 Fiber fractions 0-0.2 mm | % | | 99.5 | 99.0 |
| FS5 Fiber fractions 0.2-0.6 mm | % | | 0.4 | 0.8 |
| FS5 Fiber fractions 0.6-1.2 mm | % | | 0.0 | 0.1 |
| FS5 Fiber fractions 1.2-2.0 mm | % | | 0.0 | 0.0 |
| FS5 Fiber fractions 2.0-3.2 mm | % | | 0.0 | 0.0 |
| FS5 Fiber fractions 3.2-7.6 mm | % | | 0.0 | 0.0 |
| Particle width of fraction 0-0.2 mm | μm | | 4.3 | 4.4 |
| Particle width of fraction 0.2-0.6 mm | μm | | 25.0 | 19.0 |
| Particle width of fraction 0.6-1.2 mm | μm | | 11.7 | 15.5 |
| Particle width of fraction 1.2-2.0 mm | μm | | 13.0 | 46.4 |
| Particle with of fraction 2.0-3.2 mm | μm | | | |
| Particle width of fraction 3.2-7.6 mm | μm | | | |
| FS5 Mass fractions 0-0.2 mm | % | | 88.7 | 87.0 |
| FS5 Mass fractions 0.2-0.6 mm | % | | 11.2 | 11.1 |
| FS5 Mass fractions 0.6-1.2 mm | % | | 0.2 | 0.8 |
| FS5 Mass fractions 1.2-2.0 mm | % | | 0.0 | 1.2 |
| FS5 Mass fractions 2.0-3.2 mm | % | | 0.0 | 0.0 |
| FS5 Mass fractions 3.2-7.6 mm | % | | 0.0 | 0.0 |
| FS5 Number of pictures (avg of 3) | pcs | | 639 | 644 |
| FS5 Number of particles (avg of 3) | pcs | | 117076 | 106621 |

Example 13

In this example a soluble carbohydrate fraction and solid fraction are produced.

*Eucalyptus* wood chips were pretreated in one-step autohydrolysis and steam explosion process with two different process conditions to dissolve hemicellulose. The formed pretreated lignocellulose materials were washed with hot water in laboratory to remove most of the water soluble compounds. These remaining, water soluble compound free solids were measured with two different particle size analyzer. The results of Metso FS5 and Coulter LS230 are presented in table 6 'two water insoluble solids of pretreated *eucalyptus* based lignocellulose materials'.

TABLE 6

| | Unit | Material 1 | Material 2 |
|---|---|---|---|
| FS5 Length weighted fiber length Lc(l) ISO | mm | 0.332 | 0.462 |
| FS5 Fiber width | μm | 16.2 | 21.8 |
| FS5 Fines | % | 98.6 | 86.8 |
| FS5 Fines (Flakes) | % | 94.6 | 66.9 |
| FS5 Fines (Fibrils) | % | 0.0 | 0.0 |
| Population based particle length Lc(n) | mm | 0.018 | 0.026 |
| Length weighted particle length Lc(l) | mm | 0.031 | 0.099 |
| Weight weighted particle length Lc(w) | mm | 0.099 | 0.383 |
| FS5 Fiber fractions 0-0.2 mm | % | 98.6 | 86.8 |
| FS5 Fiber fractions 0.2-0.6 mm | % | 1.3 | 9.6 |
| FS5 Fiber fractions 0.6-1.2 mm | % | 0.1 | 3.6 |
| FS5 Fiber fractions 1.2-2.0 mm | % | 0.0 | 0.0 |
| FS5 Fiber fractions 2.0-3.2 mm | % | 0.0 | 0.0 |
| FS5 Fiber fractions 3.2-7.6 mm | % | 0.0 | 0.0 |
| Particle width of fraction 0-0.2 mm | μm | 5.9 | 7.9 |
| Particle width of fraction 0.2-0.6 mm | μm | 16.3 | 21.1 |
| Particle width of fraction 0.6-1.2 mm | μm | 15.4 | 23.6 |
| Particle width of fraction 1.2-2.0 mm | μm | | |
| Particle with of fraction 2.0-3.2 mm | μm | | |
| Particle width of fraction 3.2-7.6 mm | μm | | |
| FS5 Mass fractions 0-0.2 mm | % | 94.2 | 52.7 |
| FS5 Mass fractions 0.2-0.6 mm | % | 5.7 | 32.3 |
| FS5 Mass fractions 0.6-1.2 mm | % | 0.2 | 15.0 |
| FS5 Mass fractions 1.2-2.0 mm | % | 0.0 | 0.0 |
| FS5 Mass fractions 2.0-3.2 mm | % | 0.0 | 0.0 |
| FS5 Mass fractions 3.2-7.6 mm | % | 0.0 | 0.0 |
| Coulter LS Particle size Mean | μm | 36.5 | 54.8 |
| Coulter LS Particle size Median | μm | 29.9 | 40.8 |
| Coulter LS Particle size Mode | μm | 72.9 | 116.3 |
| Coulter LS Particle size <50 μm | % | 70.6 | 57.0 |
| Coulter LS Particle size <25 μm | % | 43.4 | 32.6 |
| Coulter LS Particle size <10 μm | % | 19.2 | 11.6 |
| Coulter LS Particle size <5 μm | % | 10.5 | 6.5 |
| Coulter LS Particle size <2 μm | % | 4.3 | 2.8 |
| Coulter LS Particle size <1 μm | % | 1.9 | 1.1 |
| Coulter LS Particle size <0.5 μm | % | 0.8 | 0.3 |
| Coulter LS Particle size <0.3 μm | % | 0.4 | 0.1 |

The method according to the present invention is suitable in different embodiments to be used for producing the most different kinds of sugar based fractions from different raw materials.

The invention is not limited merely to the example referred to above; instead many variations are possible within the scope of the inventive idea defined by the claims.

The invention claimed is:

1. A method for increasing concentration of a water soluble carbohydrate, the method comprising:
    forming a lignocellulose material by treating raw material using a treatment including acid hydrolysis and steam explosion;
    separating a washing filtrate and a water soluble carbohydrate containing fraction from the lignocellulose material in a solid-liquid separation stage;
    recirculating a first stream including at least a part of the washing filtrate from the solid-liquid separation stage to the lignocellulose material that is subjected to the solid-liquid separation stage for increasing the concentration of the water soluble carbohydrate; and
    recirculating a second stream including at least a part of the water soluble carbohydrate containing fraction from the solid-liquid separation stage to the lignocellulose material that is subjected to the solid-liquid separation stage.

2. The method of claim 1, further comprising supplying solids, at least a part of the water soluble carbohydrate containing fraction, or a combination thereof out from the solid-liquid separation stage.

3. The method of claim 1, wherein the raw material is plant based raw material.

4. The method of claim 3, wherein the plant based raw material comprises a wood based material.

5. The method of claim 1, wherein the solid-liquid separation stage includes a filtration in which the water soluble carbohydrate containing fraction is separated and a cake is formed.

6. The method of claim 5, wherein the filtration includes pressure filtration.

7. The method of claim 5, wherein the solid-liquid separation stage further includes pressing washing water through the cake to form the washing filtrate.

8. The method of claim 7, further comprising dewatering the cake after the pressing to form a solid fraction.

9. The method of claim 1, wherein the solid-liquid separation stage includes pressure filtration, the water soluble carbohydrate being separated during a pumping and/or pressing step of the pressure filtration, the washing filtrate being separated during a washing step of the pressure filtration.

* * * * *